US009626759B2

(12) United States Patent
Bertone et al.

(10) Patent No.: US 9,626,759 B2
(45) Date of Patent: Apr. 18, 2017

(54) METHOD FOR THE AUTOMATIC RECOGNITION OF ANATOMICAL STRUCTURES IN IMAGES OBTAINED BY POSITRON EMISSION TOMOGRAPHY, SYSTEM AND COMPUTER PROGRAM FOR PERFORMING SAID METHOD

(71) Applicant: DIXIT S.r.l., Turin (IT)

(72) Inventors: Elisa Bertone, Turin (IT); Piergiorgio Cerello, Turin (IT); Stephane Chauvie, Turin (IT); Andrea Gallamini, Turin (IT); Alexandru Mihail Cristian Stancu, Turin (IT)

(73) Assignee: DIXIT, S.r.l., Turin (IT)

( * ) Notice: Subject to any disclaimer, the term of this patent is extended or adjusted under 35 U.S.C. 154(b) by 0 days.

(21) Appl. No.: 14/781,218

(22) PCT Filed: Apr. 16, 2014

(86) PCT No.: PCT/IB2014/060758
§ 371 (c)(1),
(2) Date: Sep. 29, 2015

(87) PCT Pub. No.: WO2014/170838
PCT Pub. Date: Oct. 23, 2014

(65) Prior Publication Data
US 2016/0055633 A1    Feb. 25, 2016

(30) Foreign Application Priority Data

Apr. 17, 2013  (IT) .............................. TO2013A0306

(51) Int. Cl.
*G06K 9/00* (2006.01)
*A61B 6/00* (2006.01)
(Continued)

(52) U.S. Cl.
CPC ............ *G06T 7/0012* (2013.01); *A61B 6/037* (2013.01); *A61B 6/50* (2013.01); *G06T 7/004* (2013.01);
(Continued)

(58) Field of Classification Search
CPC ................ G06K 9/00; G06T 7/00; A61B 6/00
(Continued)

(56) References Cited

U.S. PATENT DOCUMENTS 7,876,938 B2 *  1/2011  Huang ................... G06T 7/0028
                                                    382/128
8,467,856 B2 *  6/2013  Renisch ............... A61B 6/5217
                                                    382/130
2006/0251307 A1  11/2006  Florin et al.

FOREIGN PATENT DOCUMENTS

WO    2007099525 A2    9/2007
WO    2010005969 A2    1/2010

OTHER PUBLICATIONS

Chung T M et al: "Intermodality registration and fusion of liver images for medical diagnosis", Intelligent Information Systems, 1997. IIS '97. Proceedings Grand Bahama Island, Bahamas Dec. 8-10, 1997, Los Alamitos, CA, USA, IEEE Comput. Soc, US.
(Continued)

*Primary Examiner* — Abolfazl Tabatabai
(74) *Attorney, Agent, or Firm* — Arent Fox LLP; Michael Fainberg

(57) ABSTRACT

A method is described for automatic recognition of anatomical structures in images obtained by position emission tomography, comprising the steps of: acquiring a 3D matrix of standardized uptake values, SUVs, associated with a plurality of PET pixels in an anatomic volume of patient; calculating the Jacobian matrix of the matrix of standardized uptake values, SUVs, projections, in a predetermined anatomical direction, of the matrix of standardized uptake
(Continued)

values, SUVs, or of its Jacobian matrix on an anatomic reference plane; locating a two-dimensional minimum of the matrix of standardized uptake values, SUVs, or of its Jacobian matrix, projected on the anatomic reference plane; locating a one-dimensional minimum in the anatomic direction of projection, corresponding to the coordinates of the two-dimensional minimum located on the reference anatomic plane of projection; and determining a center of gravity of the anatomical structure according to the coordinates of said two-dimensional and one-dimensional minima.

12 Claims, 10 Drawing Sheets

(51) Int. Cl.
| | | |
|---|---|---|
| | *G06T 7/00* | (2017.01) |
| | *G06T 7/60* | (2017.01) |
| | *A61B 6/03* | (2006.01) |
| | *A61B 5/05* | (2006.01) |

(52) U.S. Cl.
CPC ............ *G06T 7/0081* (2013.01); *G06T 7/606* (2013.01); *G06T 2207/10104* (2013.01); *G06T 2207/30004* (2013.01)

(58) Field of Classification Search
USPC ....... 382/128, 129, 130, 131, 132, 133, 134; 378/4, 8, 21–27, 901; 600/407, 410, 411, 600/425, 427
See application file for complete search history.

(56) References Cited

OTHER PUBLICATIONS

Assessing Tumor Response to Therapy, by Wolfgang A. Weber; The Journal of Nuclear Medicine, vol. 50, No. 5 (Suppl.), May 2009.
From Recist to Percist: Evolving Considerations for PET Response Criteria in Solid Tumors, by Richard L. Wahl, Heather Jacene, Yvette Kasamon, and Martin A. Lodge; The Journal of Nuclear Medicine, vol. 50, No. 5 (Suppl.), May 2009.
International Search Report for PCT/IB2014/060758, Sep. 24, 2014.
Written Opinion for PCT/IB2014/060758.

* cited by examiner

METHOD FOR THE AUTOMATIC RECOGNITION OF ANATOMICAL STRUCTURES IN IMAGES OBTAINED BY POSITRON EMISSION TOMOGRAPHY, SYSTEM AND COMPUTER PROGRAM FOR PERFORMING SAID METHOD

FIELD OF TECHNOLOGY

The present invention relates to diagnostic investigation techniques for images and more specifically it relates to a method for automatic recognition of anatomical structures in images obtained by positron emission tomography.

BACKGROUND

Positron emission tomography is a non-invasive diagnostic investigation technique for images, based on acquisition of images of the body (or of an anatomical region being examined) of a patient who has been administered a radiopharmaceutical including a tracer radionuclide with short half-life, which is a positron emitter, bound to biologically active vector molecules. The images are acquired using suitable equipment (PET, *Positron Emission Tomography*, scanner) that detects pairs of gamma photons, originating from the annihilation of the positrons emitted with electrons.

The PET images make it possible to describe the position and evaluate the intensity of the biochemical processes within a patient's tissues.

SUMMARY

The present invention generally relates to images obtained by positron emission tomography independently of the type of tracer/radiopharmaceutical that is used. By way of example, fluorodeoxyglucose positron emission tomography (FDG-PET) is a special technique of diagnostic investigation for images of the body of a patient who has been administered a positron-emitting radionuclide bound to biologically active molecules of FDG, for the purpose of studying their metabolic processes in tissues. This investigational technique has excellent diagnostic accuracy and is used in particular in oncology for staging, restaging and follow-up of numerous oncologic diseases.

The intensity of a patient's metabolic activity can be measured by an index called SUV (Standardized Uptake Value), which essentially represents the ratio of the concentration of the radioactivity in the tissue (organ) under examination to the total radioactivity administered, for every pixel or for a region of interest in an image.

The SUV is defined by the following expression:

$$SUV = \frac{[A_{PET}] \cdot \text{bodyweight}}{(A_{inj} \cdot \exp(\Delta t_{res}/\tau - A_{res}) \cdot \exp(\Delta t_{upt}/\tau)}$$

where:

$A_{PET}$ is the concentration of radioactivity in the tissues at the time t of acquisition of the PET images (expressed in MBq/kg) and is measured directly by a PET scanner in a manner known per se;

$A_{inj}$ is the dose of radiopharmaceutical (expressed in MBq) administered to the patient and measured at the moment of administration by means of a dose calibrator known per se;

$A_{res}$ is the residual activity (expressed in MBq) of radiopharmaceutical not administered to the patient and is measured by means of a dose calibrator known per se, $A_{res}$ being measured at the time $t_{res}$ after injection in the patient;

$t_{opt}$ is the time that elapses between administration of the radiopharmaceutical to the patient and acquisition of the PET image;

$\tau$ is the decay constant of the radionuclide administered to the patient and used for performing PET, and is determined analytically;

bodyweight is the patient's weight expressed in kg and is measured with bathroom scales known per se.

Fluorodeoxyglucose PET (FDG-PET) is able to record the metabolism of various organs and tissues in the human body and in particular detect the presence of tumour cells (and more generally, lesions) with an overall accuracy higher than the conventional radiological imaging techniques, such as computed tomography (CT) or magnetic resonance (MR).

Some organs of the human body have a physiological metabolism that is normally visualized in PET images, so that these are selected as reference for reporting a PET examination. For example, comparison of the uptake in a lesion relative to the uptake in the liver or in the mediastinal blood pool is used in some international guidelines for evaluating the patient's response to chemotherapy, as described in "*Assessing Tumor Response to Therapy*", by Wolfgang A. Weber, or in "*From RECIST to PERCIST: Evolving Considerations for PET Response Criteria in Solid Tumors*", by Richard L. Wahl, Heather Jacene, Yvette Kasamon, and Martin A. Lodge, both of which appeared in THE JOURNAL OF NUCLEAR MEDICINE, Vol. 50, No. 5 (Suppl.), May 2009.

Other organs as well, for example the brain and the heart, can easily be visualized in PET images since they concentrate glucose considerably, but the pattern of uptake varies from patient to patient. Organs such as the kidneys and the bladder are also easily visible in PET images, but reflect the FDG excretory activity, which varies considerably from patient to patient and depends, for example, on having urinated before the examination.

A first step in enabling the SUV to be used as a parameter for a semiquantitative analysis and for comparing SUVs obtained from the same patient at different times (longitudinal analysis) or between different patients (transversal analysis) consists of performing a calibration of all the measuring instruments that are used for measuring the quantities that appear in the above formula and of assigning an error to them.

Using a phantom devised by the same applicant, comprising a substantially cylindrical body with a cross-section with a convex curvilinear profile and containing a plurality of spheres filled with a solid matrix of germanium 68, it is possible to check the calibration of a PET scanner simply, quickly and efficiently, without requiring the manual intervention of an operator that would expose it to risks of contamination.

Following calibration, for performing a PET analysis, raw data are then acquired in the form of sinograms by carrying out a PET-CT examination that is known per se on the patient. The sinograms are reconstructed using iterative algorithms, known per se, and applying optional predetermined corrections to the data acquired. The sinograms must be reconstructed using the standard parameters recommended by the manufacturers of scanners for PET-CT for forming PET images.

The PET images are then processed in a manner known per se, obtaining some of the values of the parameters to be used according to the above equation for calculating the patient's SUV, including the concentration of radioactivity in the tissues at the time of image acquisition. The values of the other parameters required for completing the calculation of the patient's SUV, for example his weight, the dose of radiopharmaceutical administered to the patient and the residual activity of radiopharmaceutical not administered, the time elapsed between administration of the radiopharmaceutical to the patient and acquisition of the PET image, and the decay constant of the radioisotope administered to the patient, are measured by conventional techniques or are known a priori.

The SUV is then calculated for a region of interest of the patient.

Disadvantageously, in the prior art, recognition of an anatomical structure is not carried out concomitantly on the basis of the SUV values calculated from the parameters obtained from the PET images, but is left to the experience of an operator, on the basis of the visual representation supplied by the PET investigation system in the principal anatomic planes.

The aim of the present invention is to provide a method for automatic recognition of anatomical structures in a PET image.

Another aim of the invention is to provide a method for automatic measurement of the mean of the SUV of anatomical structures, for example anatomical structures recognized automatically, and the standard deviation thereof.

A further aim of the present invention is to recognize specifically, and automatically, a patient's liver in a PET image and to measure, still automatically, the mean of the SUV of the liver and the standard deviation thereof.

Still another aim of the present invention is to provide the denominator for semiquantitative indexes that may be used as an aid to the diagnostic process, e.g. providing the ratio of the uptake of a specific area, indicating a lesion, to the uptake of the reference organ, for example the liver.

According to the present invention, these aims are achieved with a method for automatic recognition of anatomical structures having the features claimed in Claim 1.

Particular embodiments form the subject matter of the dependent claims, the contents of which are to be regarded as an integral part of the present description.

The invention further relates to a system and a computer program or group of computer programs adapted to execute a method for automatic recognition of anatomical structures, as well as a method for identifying increased uptake areas representing a possible lesion in an anatomical structure, as claimed.

BRIEF DESCRIPTION OF THE DRAWINGS

Further features and advantages of the invention will be explained in more detail in the following detailed description of one embodiment thereof, given as a non-limiting example, referring to the appended drawings, in which.

DETAILED DESCRIPTION

Figure 1:
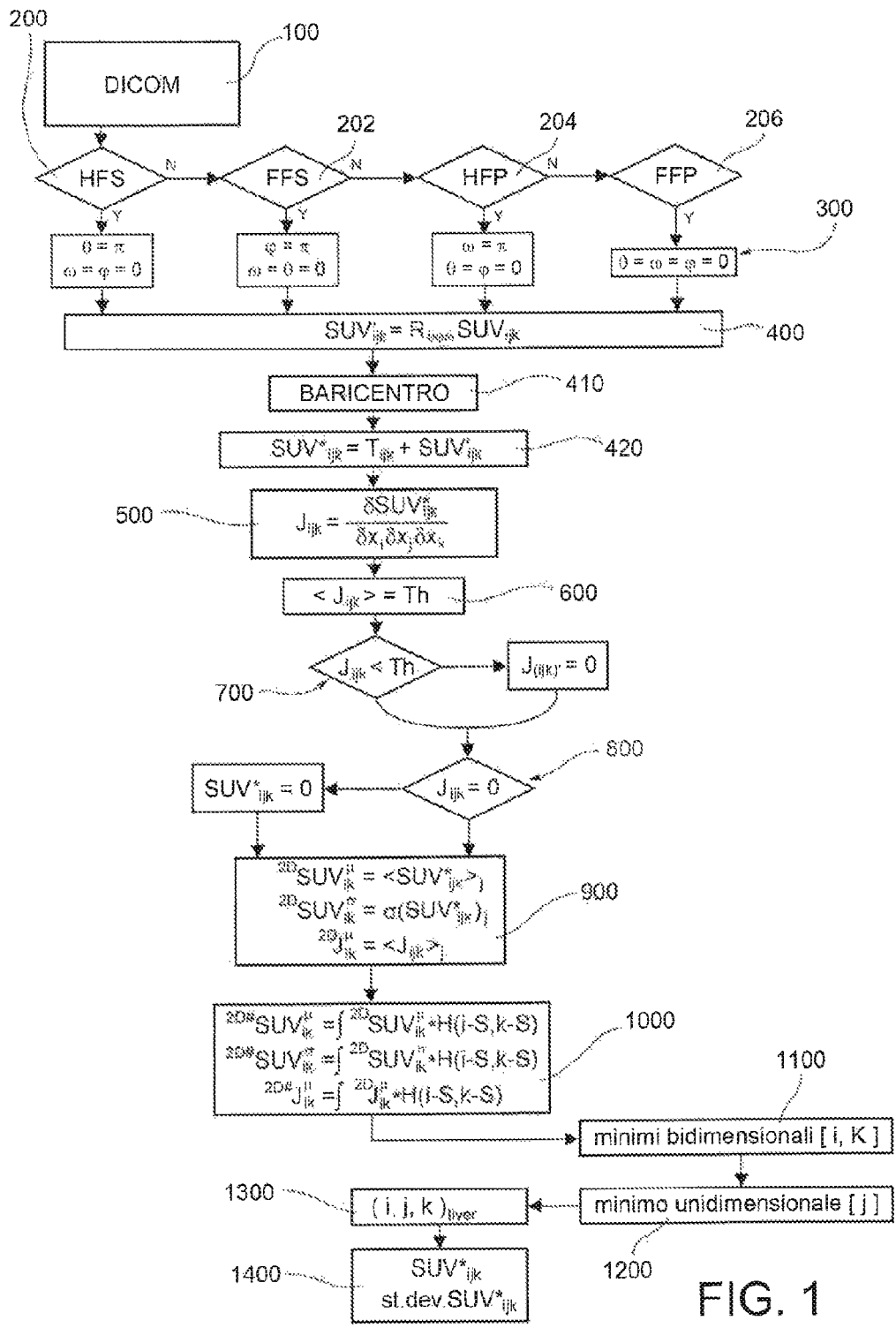
FIG. 1 is a flowchart of a method for automatic recognition of anatomical structures in images obtained by a PET scanner and for the measurement of the mean and standard deviation of the SUV of a recognized anatomical structure.

Referring to the flowchart in FIG. 1, a method is described below for automatic recognition of anatomical structures in images obtained by a PET scanner and for measuring the mean SUV in the volume of the aforementioned anatomical structure thus recognized, in which the method is applied, purely as a non-limiting example, to a patient's liver.

In step 100, a 3D matrix of data, $PIXEL_{ijk}$, representing the contents of the PET images, in which the data include for example the dimensions of each pixel, the thickness of the volume subtended at the pixel and the detected value of the SUV, at the space coordinates i,j,k identified with reference to a predetermined origin of the principal axes of the patient, i.e. of the longitudinal, sagittal and transverse axes, is acquired as a DICOM file (Digital Imaging and COmmunications in Medicine, the standard that defines the criteria for the communication, visualization, storing and printing of information of a biomedical type, for example radiological images).

Figure 2:
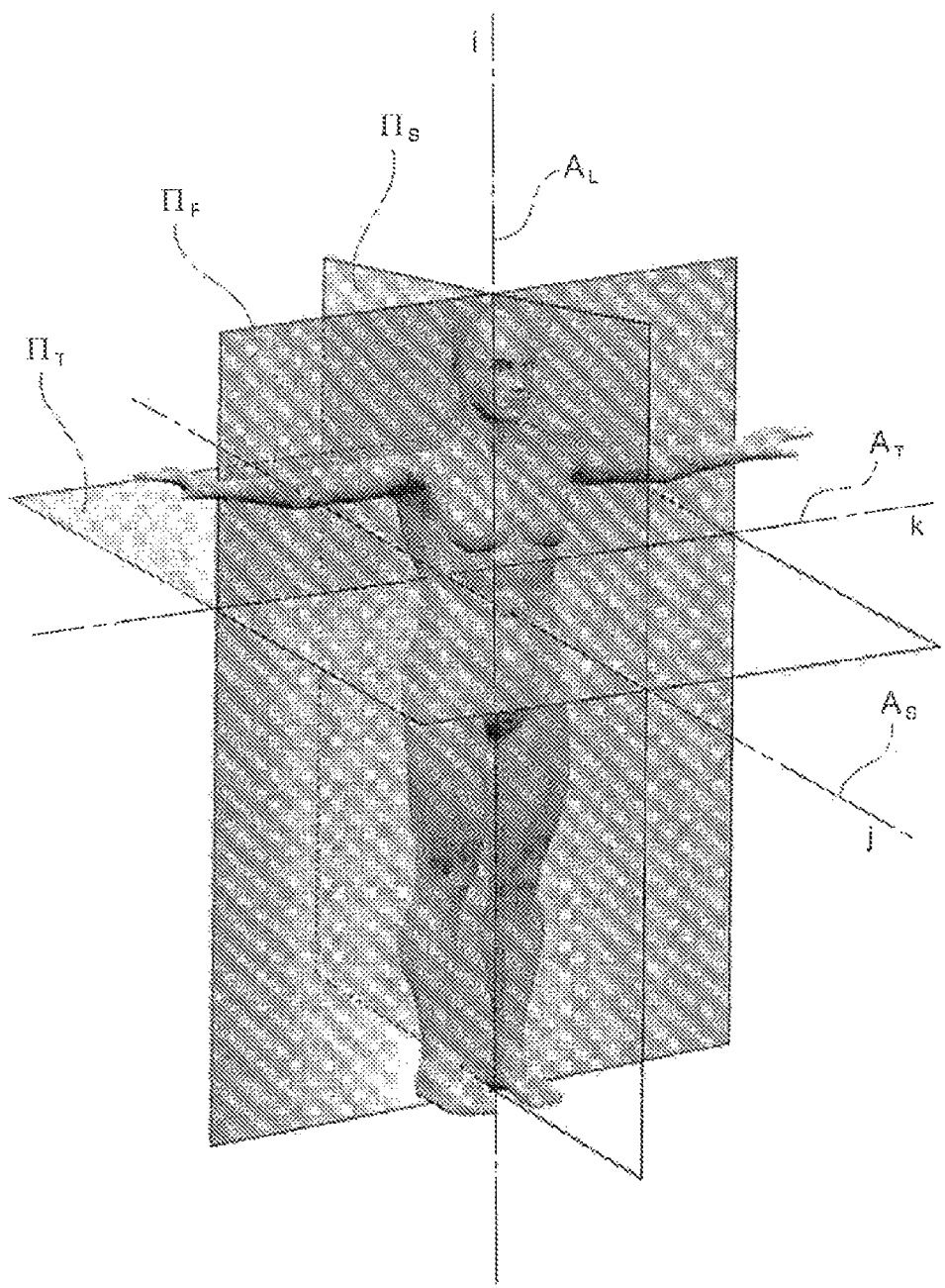
FIG. 2 shows a patient's anatomic planes and principal axes.

FIG. 2 shows the anatomic planes and the principal axes of a patient, used in the following of the description. The sagittal plane is labelled $\Pi_S$, the frontal or coronal plane is labelled $\Pi_F$, and the transverse plane is labelled $\Pi_T$. The longitudinal axis (coordinate i) is labelled $A_L$, the sagittal axis (coordinate j) is labelled $A_S$, and the transverse axis (coordinate k) is labelled $A_T$.

Figures 3A, 3B:
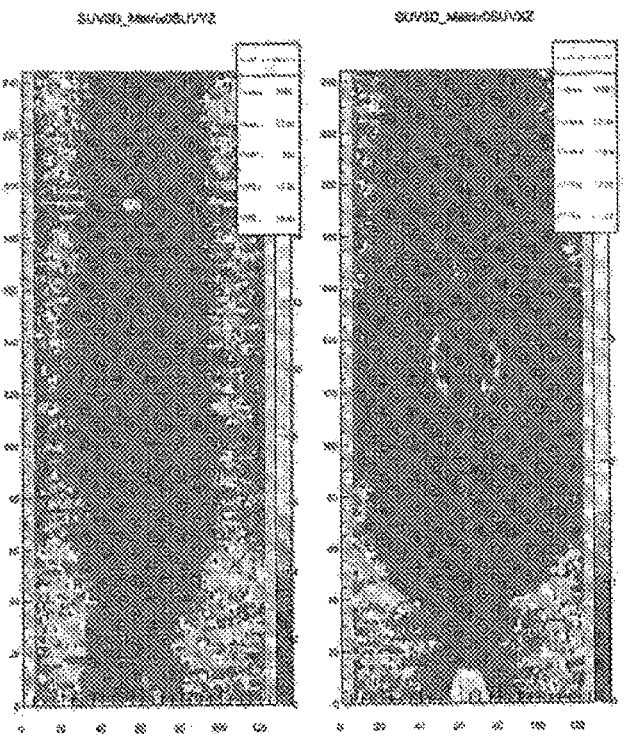
FIGS. 3a, 3b and 3c are diagrams representing a 3D matrix of a patient's SUV, processed from PET images, in a sagittal, coronal and axial section of the patient, respectively.
Figure 3C:
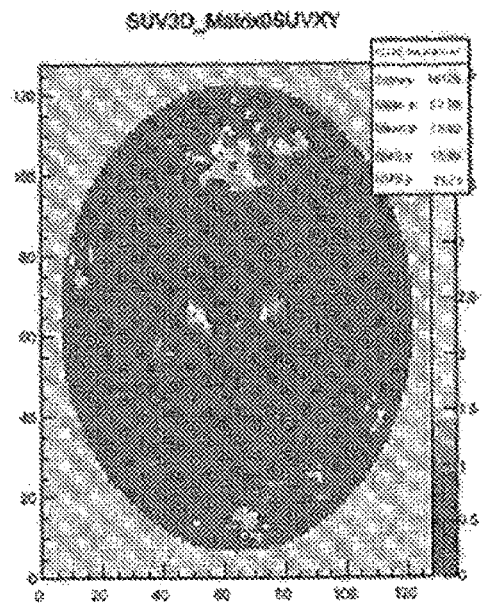

FIGS. 3a, 3b and 3c are diagrams representing a 3D matrix of a patient's SUV, processed from PET images, in a sagittal, coronal and axial section of the patient, respectively.

Advantageously, from the header of the same DICOM file, some tags indicative of the position and orientation of the patient's image are extracted for reconstructing the 3D matrix in $SUV_{ijk}$ units in real space.

Recognition of the patient's position and orientation is performed in steps 200, 202, 204, 206, where it is respectively checked whether the patient is represented in head first-supine (HFS) position, in feet first-supine (FFS) position, in head first-prone (HFP) position or in feet first-prone (FFP) position.

Depending on the patient's position and orientation, the polar coordinates $\theta$, $\phi$, $\omega$ indicating the rotation required for bringing the image into a predetermined reference position, for example the feet first-prone (FFP) position, are calculated in step 300.

Then a rotation and translation of the SUV matrix (i.e. of the matrix of elements $SUV_{ijk}$) is preferably carried out for co-registration of all patients in the same position, standing with their head high, with the origin of the reference system at the patient's geometric centre of mass.

The rotation-translation comprises in particular a rotation $$SUV'_{ijk} = R_{\theta\phi\omega} SUV_{ijk}$$

in step 400, in which $R_{\theta\phi\omega}$ represents the rotation matrix, a function of the variables $\theta$, $\phi$, $\omega$ calculated in step 300, calculation of the patient's geometric centre of gravity in step 410, and a translation $$SUV^*_{ijk} = T_{ijk} + SUV'_{ijk}$$

along the principal axes of the patient in step 420, in which $T_{ijk}$ represents the translation matrix.

Figures 4A, 4B:
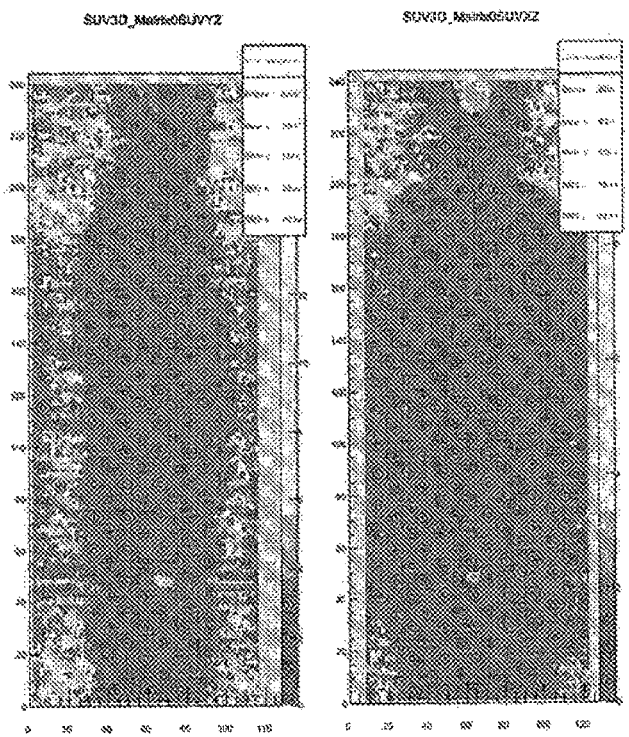
FIGS. 4a, 4b and 4c are diagrams representing the 3D matrix of FIGS. 3a, 3b, 3c of a patient's SUV, rotated and translated, in a sagittal, coronal and axial section of the patient, respectively.
Figure 4C:
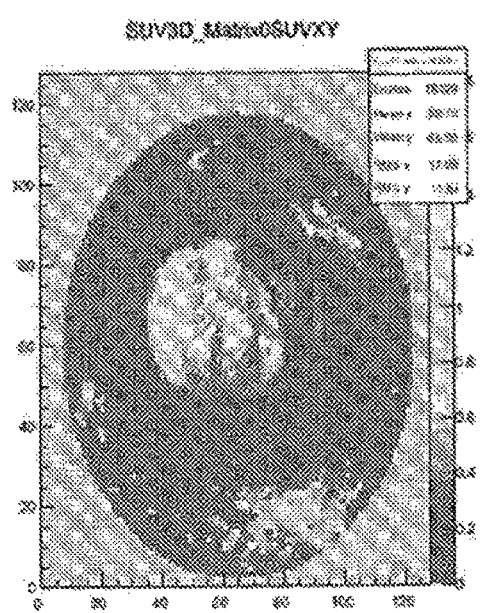

FIGS. 4a, 4b and 4c are diagrams representing the 3D matrix of FIGS. 2a, 2b, 2c of a patient's SUV, rotated and translated, in a sagittal, coronal and axial section of the patient, respectively.

Next, in step 500, the Jacobian matrix $J_{ijk}$ of the matrix $SUV^*_{ijk}$ $$J_{ijk} = \frac{\partial SUV^*_{ijk}}{\partial x_i \partial x_j \partial x_k}$$

is calculated for the purpose of identifying the isotropic variation of the SUV of each pixel relative to the SUV of the adjacent pixels, in the three spatial directions of the reference system.

Figures 5A, 5B:
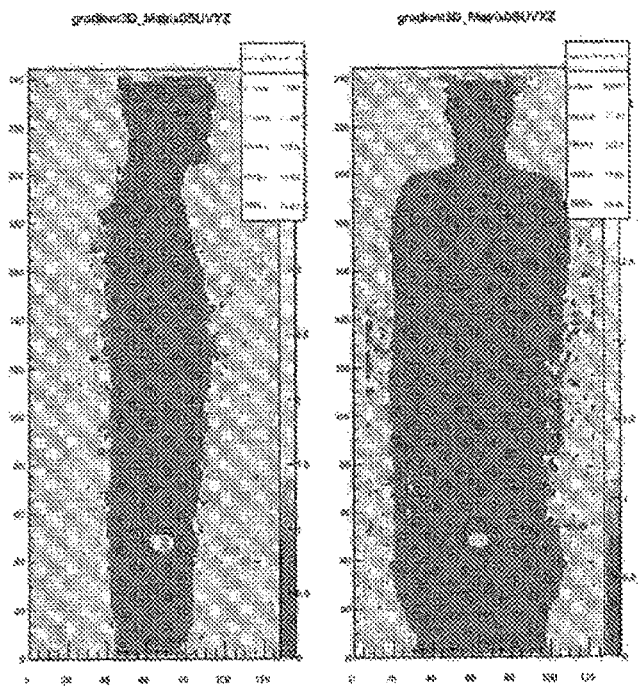
FIGS. 5a, 5b and 5c are diagrams representing the Jacobian matrix of a patient's SUV, calculated from the 3D matrix of FIGS. 4a, 4b and 4c, in a sagittal, coronal and axial section of the patient, respectively.
Figure 5C:
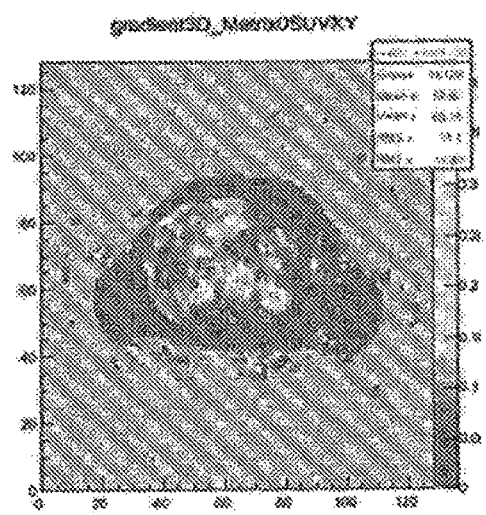

FIGS. 5a, 5b and 5c are diagrams representing the Jacobian matrix of a patient's SUV, calculated from the 3D matrix of FIGS. 4a, 4b and 4c, in a sagittal, coronal and axial section of the patient, respectively.

Then, a background value of the Jacobian matrix of the SUV, i.e. a value of the Jacobian matrix of the SUV corresponding to at least one pixel outside the region of the patient's body, is determined in step 600. This value, indicated Th hereinafter, is assigned a threshold function. This is preferably obtained by calculating the mean value of the Jacobian $$\langle J_{ijk} \rangle = Th$$

in at least one volume outside the patient's body, for example a toroidal volume around the patient's head, and preferably in two cubic volumes of predetermined side 1, for example equal to 5 cm, positioned outside the patient's body, within the region of the head.

In the next step 700, preferably a masking algorithm is applied, for which, starting from the longitudinal axis of the image of the patient and for each transverse plane of the image in the radial direction, i.e. from top to bottom and from the centre towards the periphery of the patient's body, the value 0 is assigned to all the pixels of $J_{ijk}$ after that for which the condition $J_{ijk} > Th$ ceases to apply, i.e. $J_{(ijk)'} = 0$ is imposed for each pixel (ijk)' adjacent to the pixel (ijk) in any direction, where the relation of adjacency synthetically labelled with (ijk)' indicates indifferently the pixels (i'jk), (ij'k) and (ijk'), the symbol "'" (prime) referring to the adjacent discrete coordinate along one of the principal axes of the image.

Consequently, in step 800, masking is preferably applied to the matrix $SUV^*_{ijk}$, imposing the value 0 on all the values of the matrix $SUV^*_{ijk}$ for which the above condition is satisfied, i.e. $J_{ijk} = 0$.

At least one anteroposterior projection of both matrices $SUV^*_{ijk}$ and $J_{ijk}$ on the coronal plane, and preferably a plurality of projections, is/are calculated in step 900.

The projections are preferably calculated according to the expressions given below:

$$^{2D}SUV^\mu_{ik} = \langle SUV^*_{ijk} \rangle_j \quad \text{a.}$$

$$^{2D}SUV^\sigma_{ik} = \sigma(SUV^*_{ijk})_j \quad \text{b.}$$

$$^{2D}J^\mu_{ik} = \langle J_{ijk} \rangle_j \quad \text{c.}$$

where the left superscript "2D" indicates that it is a matrix of values of a two-dimensional matrix, indicated with subscript ik if the projection takes place in the direction j (parallel to the sagittal axis).

Specifically, the projection $^{2D}SUV^\mu_{ik}$ is obtained by calculating the mean value of the matrix of the SUV along the preferential direction indicated, the projection $^{2D}SUV^\sigma_{ik}$ is obtained by calculating the standard deviation of the matrix of the SUV along the preferential direction indicated, and the projection $^{2D}J^\mu_{ik}$ is obtained by calculating the mean value of the Jacobian matrix of the SUV along the preferential direction indicated.

Figures 6A, 6B:
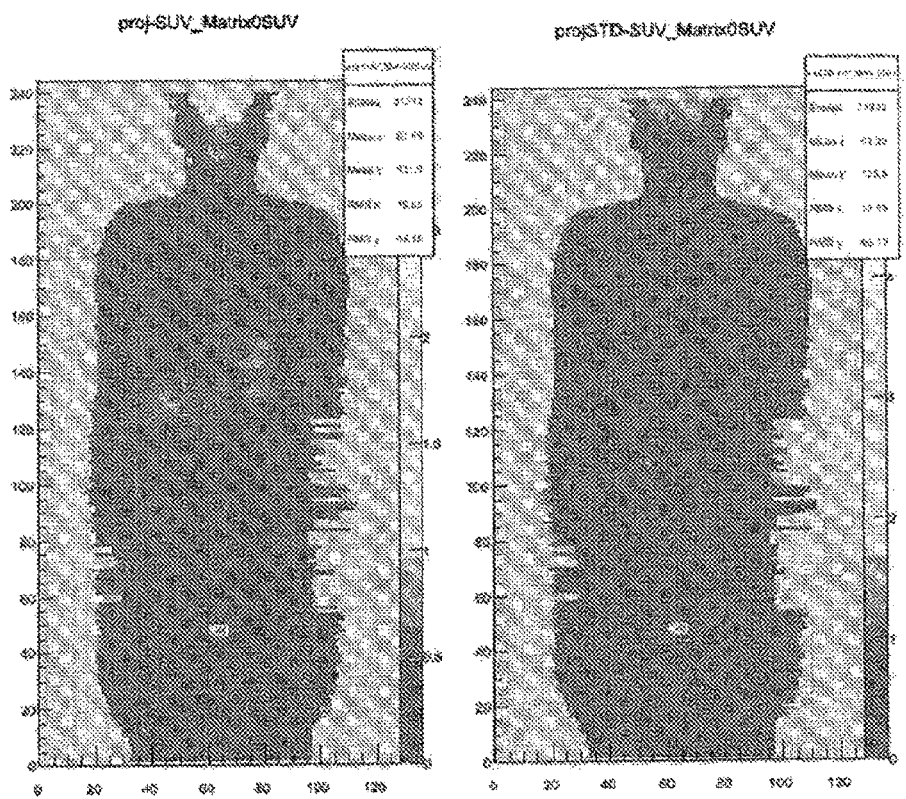
FIGS. 6a and 6b are projections of the matrix of a patient's SUV in the sagittal direction (on the coronal plane), respectively as mean and standard deviation of the SUV values in the pixels aligned in sagittal directions.
Figure 7:
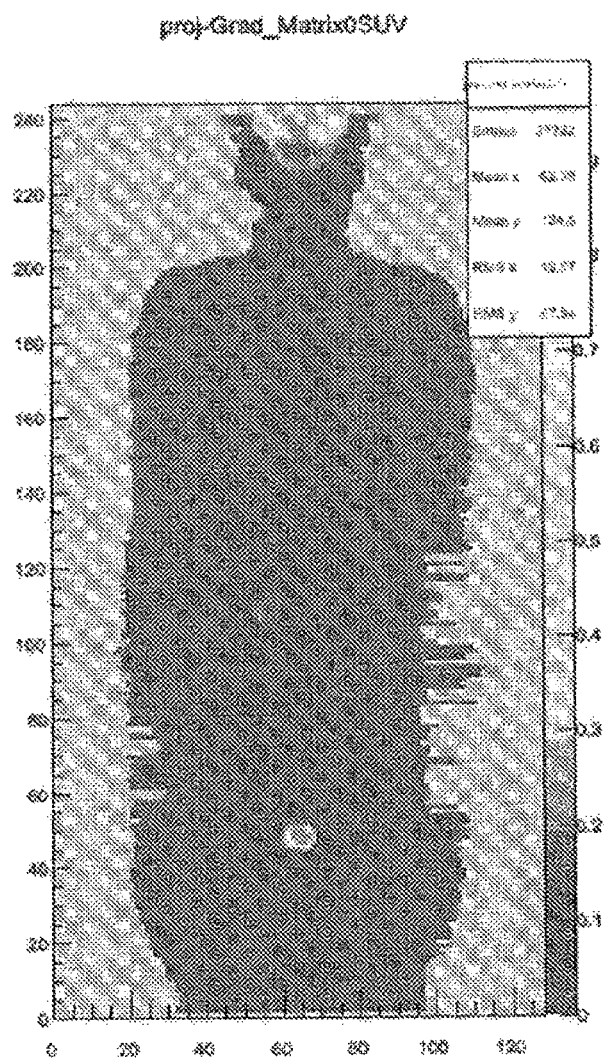
FIG. 7 is a projection of the Jacobian matrix of a patient's SUV in the sagittal direction (on the coronal plane), as mean of the SUV values in the pixels aligned in sagittal directions.

FIGS. 6a and 6b are projections of the matrix of a patient's SUV in the sagittal direction, $^{2D}SUV^\mu_{ik}$, $^{2D}SUV^\sigma_{ik}$, respectively as mean value ($\langle SUV^*_{ijk} \rangle_j$) and standard deviation ($\sigma(SUV^*_{ijk})_j$). FIG. 7 is a projection of the Jacobian matrix of a patient's SUV in the sagittal direction, $^{2D}J^\mu_{ik}$, as mean value ($\langle J_{ijk} \rangle_j$).

In step 1000, preferably a sampling is carried out of the projections $^{2D}SUV^\mu_{ik}$, $^{2D}SUV^\sigma_{ik}$, $^{2D}J^\mu_{ik}$, indicated with $^{2D\#}SUV^\mu_{ik}$, $^{2D\#}SUV^\sigma_{ik}$ and $^{2D\#}J^\mu_{ik}$, with a pitch S of predetermined dimensions, for example 5 cm, in the longitudinal and transverse directions. In the figure, sampling is indicated by the operation of convolution of the respective two-dimensional matrices with the function H, the Heaviside unit function.

The sampling operation is preferably carried out for the purpose of identifying the regions of greater homogeneity.

To improve the accuracy of the operation, the edge pixels of the image, which might falsify the calculations, are not taken into account.

Figures 8A, 8B, 8C:
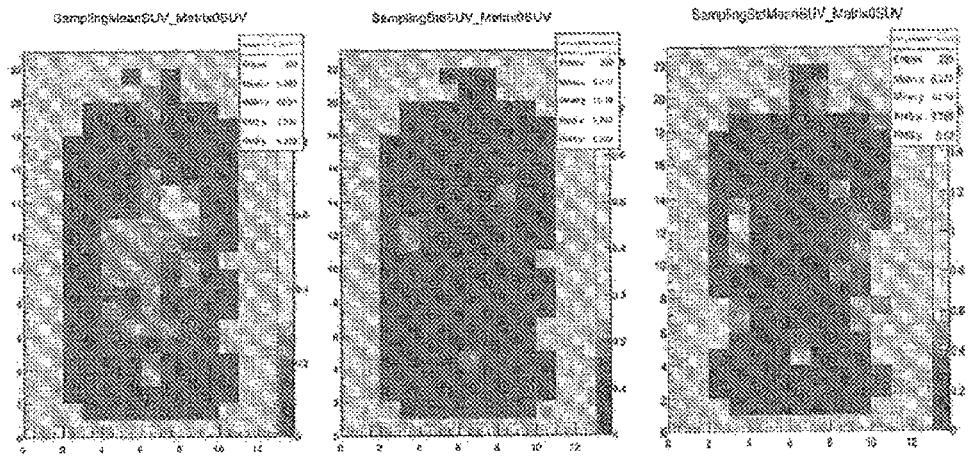
FIGS. 8a, 8b and 8c are diagrams representing a sampling of the matrix of the SUV projected on the coronal plane using the mean of the SUV values in the pixels aligned in sagittal directions, in which the sampling is obtained respectively as a mean of the mean of the SUV values, as a mean of the standard deviation of the SUV values, as a mean of the ratio of the standard deviation to the mean of the SUV values.

FIGS. 8a, 8b and 8c are diagrams representing a sampling of the matrix of the SUV projected on the coronal plane using the mean of the SUV values in the pixels aligned in sagittal directions, in which the sampling is obtained respectively as mean of the mean of the SUV values, standard deviation of the mean of the SUV values, and ratio of the standard deviation to the mean of the SUV values.

Figures 9A, 9B, 9C:
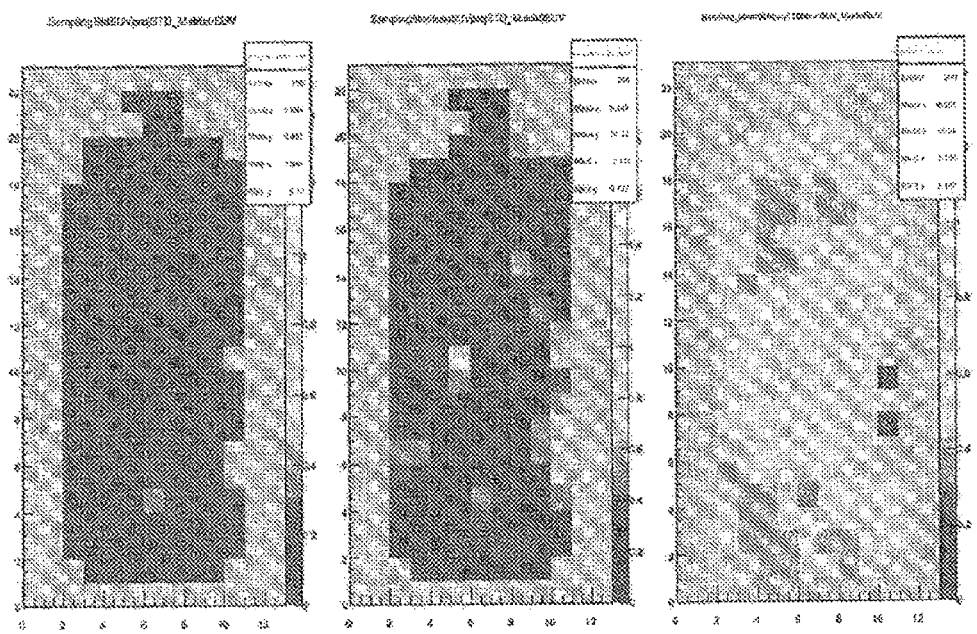
FIGS. 9a, 9b, 9c are diagrams representing the sampling of the matrix of the SUV projected on the coronal plane using the standard deviation of the SUV values in the pixels aligned in sagittal directions, in which the sampling is obtained respectively as a standard deviation of the mean of the SUV values, as a standard deviation of the standard deviation of the SUV values, as a standard deviation of the ratio of the standard deviation to the mean of the SUV values.

FIGS. 9a, 9b, 9c are diagrams representing the sampling of the matrix of the SUV projected on the coronal plane using the standard deviation of the SUV values in the pixels aligned in sagittal directions, in which the sampling is obtained respectively as standard deviation of the mean of the SUV values, standard deviation of the standard deviation of the SUV values, standard deviation of the ratio of the standard deviation to the mean of the SUV values.

Figures 10A, 10B, 10C:
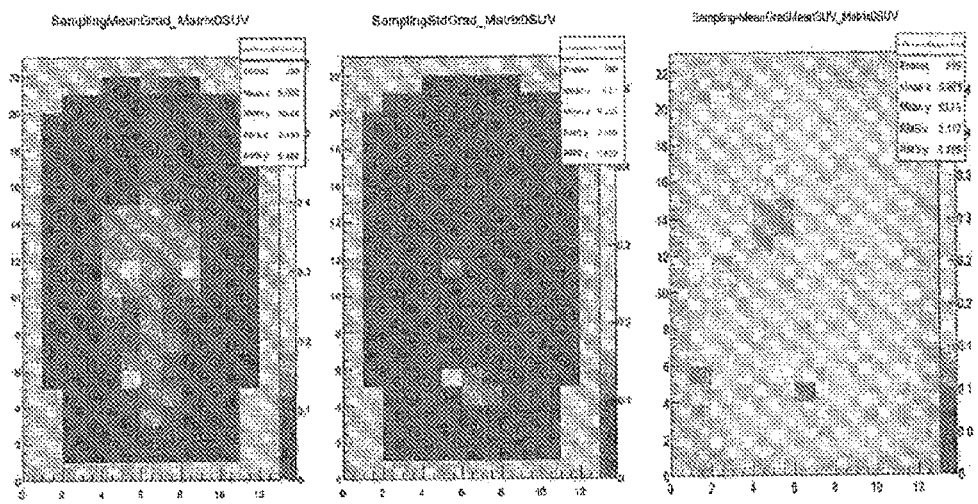
FIGS. 10a, 10b and 10c are diagrams representing the sampling of the Jacobian matrix of the SUV projected on the coronal plane using the mean in sagittal directions, in which the sampling is obtained respectively as a mean of the values of the Jacobian matrix, standard deviation of the values of the Jacobian matrix and ratio of the mean of the values of the Jacobian matrix to the mean of the SUV values.

FIGS. 10a, 10b and 10c are diagrams representing the sampling of the Jacobian matrix of the SUV projected on the coronal plane using the mean in sagittal directions, in which the sampling is obtained respectively as mean of the values of the Jacobian matrix, standard deviation of the values of the Jacobian matrix and ratio of the mean of the values of the Jacobian matrix to the mean of the SUV values.

In the projected matrices $^{2D\#}SUV^{\mu}_{ik}$, $^{2D\#}SUV^{\sigma}_{ik}$ and $^{2D\#}J^{\mu}_{ik}$, a predetermined number of two-dimensional maxima and minima, for example the first ten, is identified in step 1100, associating the position i'k' with each of them and the distances of the positions i'k' from the origin of the reference system are calculated.

In the specific preferred but non-limiting application, in automatic recognition of the patient's liver, the first minimum of one of the matrices $^{2D\#}SUV^{\mu}_{ik}$, $^{2D\#}SUV^{\sigma}_{ik}$ and $^{2D\#}J^{\mu}_{ik}$ is selected, excluding the minima whose distance R from the patient's geometric centre of gravity is above a predetermined value, for example 40 cm, and its position (i,k) on the coronal plane is determined.

Clearly, in applying the method to organs other than the liver, selection of the minimum of one of the matrices $^{2D\#}SUV^{\mu}_{ik}$, $^{2D\#}SUV^{\sigma}_{ik}$ and $^{2D\#}J^{\mu}_{ik}$ is carried out by excluding the minima according to a different order relationship between distance R of the patient's geometric centre of gravity and at least a threshold value. Generally, said relationship may be based on the comparison between said distance R and a pair of thresholds at the ends of an admissibility interval, which in particular cases coincide with a minimum or with a maximum threshold, whereby in general the localized minima are admissible that have a distance from a patient's centre of gravity between a predetermined threshold interval.

Different threshold values with respect to those for application of the method to the automatic recognition of the liver may be applied in case, for example, the reference organ is positioned at a different distance from the centre of gravity. For example, for the automatic recognition of the patient's brain, selection of the minimum of one of the matrices $^{2D\#}SUV^{\mu}_{ik}$, $^{2D\#}SUV^{\sigma}_{ik}$ and $^{2D\#}J^{\mu}_{ik}$ is carried out by excluding those minima whose distance R from the patient's geometric centre of gravity is lower than a predetermined value, for example 30 cm.

From the matrices indicated by way of illustration, preferably that for which the sensitivity of the method is maximum is selected, that which is obtained by verifying the position of (i,k) manually. In this way it is possible to exclude spurious minima located in regions of the patient that are not of interest, at distances from his geometric centre of gravity incompatible with the expected distance of the region of interest (in this case, the liver).

Figures 11A, 11B, 11C:
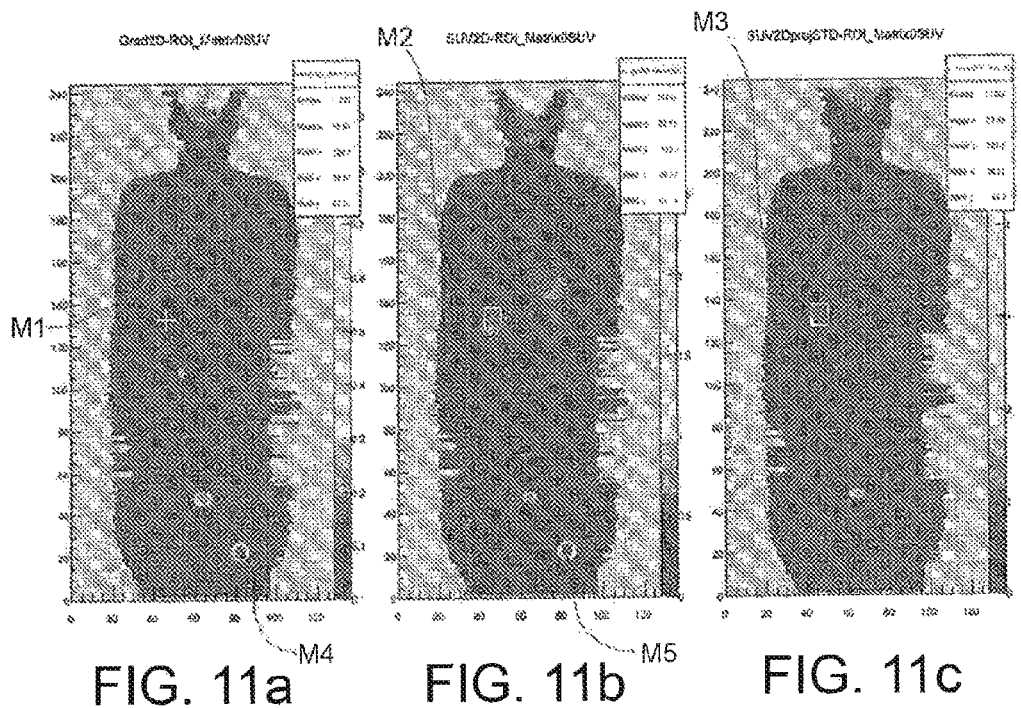
FIGS. 11a, 11b and 11c are diagrams representing the minima and maxima of some quantities of interest, in a sagittal section and on the coronal plane.

FIGS. 11a, 11b and 11c are diagrams representing the minima and maxima of some quantities of interest, in a sagittal section and on the coronal plane. Specifically, M1 indicates the minimum of the ratio of the mean of the Jacobian matrix of the SUV to the mean of the matrix of the SUV; M2 indicates the minimum of the ratio of the standard deviation of the matrix of the SUV to the mean of the matrix of the SUV; M3 indicates the minimum of the ratio of the standard deviation of the matrix of the SUV projected as standard deviation to the mean of the matrix of the SUV. Separately, the spurious minima M4 and M5 are also identified, respectively the minimum of the standard deviation of the Jacobian matrix of the SUV and the minimum of the standard deviation of the matrix of the SUV.

Next, preferably n mean values are calculated in the anteroposterior (sagittal) direction in the position (i,k) of the minimum identified in the selected matrix. The n mean values are calculated at a predetermined sampling pitch, for example equal to 5 cm. The choice of sampling pitch affects the effectiveness of sampling. Advantageously, this corresponds to approximately half the expected size of the organ under examination.

Then, in step 1200 a one-dimensional minimum is identified also in the sagittal direction (coordinate j) by calculating the minimum among the n mean values in position (i,k). Then, in step 1300, the position $(i,j,k)_{liver}$ is extracted, which thus represents a pixel included in the region of interest (volume of the liver), which is estimated to be its centre. That is, the centre of gravity of the anatomical structure under examination is determined according to the coordinates of said two-dimensional and one-dimensional minima, and preferably coincides with said coordinates.

Based on these data, it is possible to calculate, in step 1400, the mean value μ and the standard deviation σ of the standardized uptake values, SUV values, included in a volume approximating the anatomical structure having centre coinciding with said centre of gravity determined, for example a spherical volume of predetermined radius, for example equal to 5 cm, with centre at $(i,j,k)_{liver}$, for the purpose of determining the mean value and standard deviation of the SUV of the liver. The radius is suitably selected so as to incorporate, in the spherical approximation volume, the pixels, and the SUV values that definitely belong to the anatomical structure under examination (for example, the liver), without said approximation volume reaching or exceeding the confines of the organ under examination.

Advantageously, the mean value of the SUV of the liver (μ) calculated by the method described can be used, for example, for establishing whether the examination in carried out is of sufficient diagnostic quality for a quantitative analysis.

For this purpose, a reduced variable z is constructed, as:

$$z=(\mu-SUV_{liver})^2/\sigma_{liver}$$

in which the values $SUV_{liver}$ and $\sigma_{liver}$ are obtained, for example, from as large a population as desired of patients who have undergone PET scans.

Based on this, the probability α that $SUV_{liver}$ belongs to the population in question is calculated. If this is below a threshold, for example 95%, the examination is excluded from the quantitative analysis.

Alternatively, the mean of the SUV of the liver (μ) can be used for determining the areas of increased-uptake in the PET images. As taught in the articles "Assessing Tumor Response to Therapy", by Wolfgang A. Weber, and "From RECIST to PERCIST: Evolving Considerations for PET Response Criteria in Solid Tumors", by Richard L. Wahl, Heather Jacene, Yvette Kasamon, and Martin A. Lodge, which appeared in THE JOURNAL OF NUCLEAR MEDICINE, Vol. 50, No. 5 (Suppl.), May 2009, the liver is used as reference for establishing whether an area of uptake of FDG can be regarded as a lesion, i.e. pathological, or not.

A method for identifying an increased uptake area representative of a possible lesion in an anatomical structure of a patient thus comprises determining the mean value of the standardised uptake values, SUV, included in an area of the predetermined volume approximating an anatomical structure under examination, and comparing said mean value with the mean value of the standardised uptake values, SUV, of the patient's liver.

With the method described, it becomes natural to apply a method of threshold segmentation, of the prior art, using as threshold not a predetermined fixed SUV value, but the mean value of the SUV of the liver. The segmented image would then contain only those values greater than the value of the liver.

It is moreover possible to calculate the matrix $Z_{ijk}$ as:

$$Z_{ijk}=(SUV_{ijk}-\mu)^2/\sigma$$

where each pixel is replaced with its distance, in units of $\sigma$, from the value of the SUV of the liver. In this way it is possible to evaluate the different responses of a patient relative to a standard patient for a qualitative evaluation that makes it possible to distinguish a pathological condition from a general physiological condition.

To improve the specificity of the segmentation method it is moreover possible to use the method described and illustrated for the case of the liver to eliminate other organs or tissues that have a greater physiological uptake than that of the liver, for example heart, brain, kidneys and bladder, leaving only the suspected areas of disease.

Figure 12:
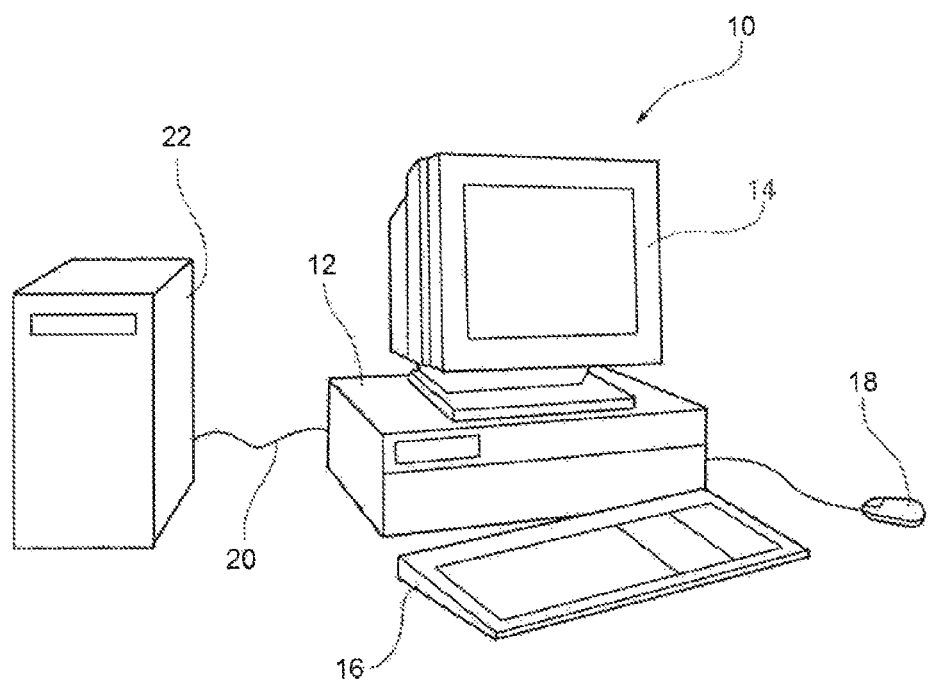
FIG. 12 shows a system for performing a method for automatic recognition of anatomical structures in images obtained by a PET scanner and for the measurement of the mean and standard deviation of the SUV of a recognized anatomical structure.

Referring to FIG. 12, a system is shown in basic outline for executing a method for automatic recognition of anatomical structures in images obtained by PET scanners, the subject of the invention. This comprises a computerized workstation 10 of a known type, having a processor subsystem 12, a visualization device (display) 14, a keyboard 16, a pointing device (mouse) 18 and a device for connecting to a local network (network bus) 20.

As the workstation, it is possible to use, for example, a personal computer having a 3.1 GHz Intel Core i5 2400 processor, RAM memory of 4 GBytes, an internal hard disk of 500 GBytes and an operating system of the Windows, Mac OS or Linux type.

The workstation is set up for executing programs stored on disk or accessible from the network, and for displaying the results on the display 14.

The system according to the invention further comprises an archiving subsystem 22 of a known type, for example connected by means of the network connection 20 to the workstation 10 and adapted to have stored databases of images (DICOM files).

Naturally, the databases can also be stored, if of limited size, in the disk unit of workstation 10 without this altering the features of the invention. Moreover, the system can be arranged for connection to other input/output peripherals, local or remote, or can consist of a processing system of the distributed type, but such solutions mentioned here are considered to be well known in the prior art and will not be described further at this point because they are not relevant per se for the purposes of implementing and understanding the present invention.

In general, the system in the configuration described or in other equivalent configurations is arranged for executing a method for automatic recognition of anatomical structures in images obtained by PET scanners based on programs or groups of programs comprising one or more modules of code for carrying out the aforementioned method, with the aid of the databases stored in the disk subsystem 22.

Naturally, without prejudice to the principle of the invention, the forms of implementation and the details of the embodiments can be varied widely compared to what has been described and illustrated purely as a non-limiting example, while remaining within the scope of protection of the present invention defined by the appended claims.

The invention claimed is:

1. Method for the automatic recognition of anatomical structures in images obtained by positron emission tomography, characterized in that it comprises the following steps:
   acquisition of a 3D matrix of data including standardized uptake values, SUVs, associated to a plurality of PET pixels in an anatomic volume of a patient;
   calculation of the Jacobian matrix of said 3D matrix of standardized uptake values, SUVs, and determination of the isotropic variation of the standardized uptake values, SUVs, of each pixel with respect to adjacent pixels, in three predefined orthogonal reference spatial directions;
   projection, along a predetermined anatomical direction of projection, of said 3D matrix of standardized uptake values, SUVs, or of said Jacobian matrix of the 3D matrix of standardized uptake values, SUVs, on an anatomical reference plane;
   location of at least one two-dimensional minimum of said matrix of standardized uptake values, SUVs, or of said Jacobian matrix of the matrix (SUVijk) of standardized uptake values, SUVs, projected onto said anatomical reference plane (ΠF), having a distance from a centre of gravity of the patient within a predetermined threshold interval;
   location of at least one one-dimensional minimum along said predetermined anatomical direction of projection, corresponding to the coordinates of said two-dimensional minimum localized on said anatomical reference projection plane; and
   determination of a centre of gravity of the anatomical structure according to the coordinates of said two-dimensional and one-dimensional minima.

2. Method according to claim 1, further comprising the acquisition of information on position and orientation of the PET pixels associated with said standardized uptake values, SUVs, and the transformation of coordinates by rotation and translation of said 3D matrix of standardized uptake values, SUVs, to bring said pixels to a predetermined reference position.

3. Method according to claim 1, comprising the selection of a subset of data of said 3D matrix of standardized uptake values, SUVs, by comparison with a predetermined threshold value of variation of the standardized uptake values, SUVS.

4. Method according to claim 3, wherein said selection is implemented by scanning said Jacobian matrix of said 3D matrix of standardized uptake values, SUVs, starting from the longitudinal axis of the image of the patient and for each transverse plane of the image in the radial direction.

5. Method according to claim 3, wherein said threshold value is an average background value of a subset of values of the Jacobian matrix of said 3D matrix of standardized uptake values, SUVs, in a predetermined image region external to the volume of the patient.

6. Method according to claim 3 any one of the preceding claims, wherein said projection is obtained by calculating the mean or the standard deviation of the values of said 3D matrix of standardized uptake values, SUVs, or of said Jacobian matrix of the 3D matrix of standardized uptake values, SUVs, along a projection direction.

7. Method according to claim 3, comprising sampling the data of the matrix of standardized uptake values, SUVs, projected on said anatomical reference plane (IIF), or of the Jacobian matrix of the matrix of standardized uptake values, SUVs, projected on said anatomical reference plane, along the orthogonal directions of said anatomical reference plane, with a predetermined pitch.

8. Method according to claim 3, wherein said one-dimensional minimum is the minimum among a plurality of mean values sampled at a predetermined pitch.

9. Method according to claim 3, comprising determining the mean value and/or the standard deviation of the uptake values of the anatomical structure by calculating the mean value and/or the standard deviation of the standardised uptake values, SUVs, in a predetermined volume approximating the anatomical structure having a centre coincident with said determined centre of gravity.

10. Processing system for the automatic detection of anatomical structures in images obtained by positron emission tomography, programmed to perform the following steps:
   acquisition of a 3D matrix of data including standardized uptake values, SUVs, associated to a plurality of PET pixels in an anatomic volume of a patient;
   calculation of the Jacobian matrix of said 3D matrix of standardized uptake values, SUVs, and determination of the isotropic variation of the standardized uptake values, SUVs, of each pixel with respect to adjacent pixels, in three predefined orthogonal reference spatial directions;
   projection, along a predetermined anatomical direction of projection, of said 3D matrix of standardized uptake values, SUVs, or of said Jacobian matrix of the 3D matrix of standardized uptake values, SUVs, on an anatomical reference plane;
   location of at least one two-dimensional minimum of said matrix of standardized uptake values, SUVs, or of said Jacobian matrix of the matrix of standardized uptake values, SUVs, projected onto said anatomical reference plane, having a distance from a centre of gravity of the patient within a predetermined threshold interval;
   location of at least one one-dimensional minimum along said predetermined anatomical direction of projection, corresponding to the coordinates of said two-dimensional minimum localized on said anatomical reference projection plane; and
   determination of a centre of gravity of the anatomical structure according to the coordinates of said two-dimensional and one-dimensional minima.

11. A non-transitory computer storage medium storing a computer program executable by a processing system, comprising one or more code modules for performing a method for the automatic recognition of anatomical structures in images obtained by positron emission tomography, comprising the following steps:
   acquisition of a 3D matrix of data including standardized uptake values, SUVs, associated to a plurality of PET pixels in an anatomic volume of a patient;
   calculation of the Jacobian matrix of said 3D matrix of standardized uptake values, SUVs, and determination of the isotropic variation of the standardized uptake values, SUVs, of each pixel with respect to adjacent pixels, in three predefined orthogonal reference spatial directions;
   projection, along a predetermined anatomical direction of projection, of said 3D matrix of standardized uptake values, SUVs, or of said Jacobian matrix of the 3D matrix of standardized uptake values, SUVs, on an anatomical reference plane;
   location of at least one two-dimensional minimum of said matrix of standardized uptake values, SUVs, or of said Jacobian matrix of the matrix of standardized uptake values, SUVs, projected onto said anatomical reference plane, having a distance from a centre of gravity of the patient within a predetermined threshold interval;
   location of at least one one-dimensional minimum along said predetermined anatomical direction of projection, corresponding to the coordinates of said two-dimensional minimum localized on said anatomical reference projection plane; and
   determination of a centre of gravity of the anatomical structure according to the coordinates of said two-dimensional and one-dimensional minima.

12. Method for identifying an increased uptake area representative of a possible lesion in an anatomical structure of a patient, comprising:
   determining the mean value of the standardised uptake values, SUVs, comprised in an area of the predetermined volume approximating the anatomical structure recognized by the method comprising the following steps:
      acquisition of a 3D matrix of data including standardized uptake values, SUVs, associated to a plurality of PET pixels in n anatomic volume of a patient;
      calculation of the Jacobian matrix of said 3D matrix of standardized uptake value, SUVs, and determination of the isotropic variation of the standardized uptake values, SUVs, of each pixel with respect to adjacent pixels, in three predefined orthogonal reference spatial directions;
      projection, along a predetermined anatomical direction of projection, of said 3D matrix of standardized uptake values, SUVs, of said Jacobian matrix of the 3D matrix of standardized uptake values, SUVs, on an anatomical reference plane;
      location of at least one two-dimensional minimum of said matrix of standardized uptake values, SUVs, or of said Jacobian matrix of the matrix of standardized uptake values, SUVs, projected onto said anatomical reference plane, having a distance from a centre of gravity of the patient within a predetermined threshold interval;
      location of at least one one-dimensional minimum along said predetermined anatomical direction of projection, corresponding to the coordinates of said two-dimensional minimum localized on said anatomical reference projection plane; and
      determination of a centre of gravity of the anatomical structure according to the coordinates of said two-dimensional and one-dimensional minima; and
   comparing said mean value of the standardised uptake values, SUVs, comprised in an area of the predetermined volume approximating the anatomical structure to the mean value of the standardised uptake values, SUVs, of the patient's liver.

\* \* \* \* \*